United States Patent [19]

Smiley

[11] Patent Number: 6,117,823
[45] Date of Patent: Sep. 12, 2000

[54] METHOD OF USING ALIPHATIC CARBOXYLIC ACID DIESTERS AS NON-SELECTIVE HERBICIDES

[75] Inventor: Robert A. Smiley, Wilmington, Del.

[73] Assignee: Dixie Chemical Company, Houston, Tex.

[21] Appl. No.: 09/162,393

[22] Filed: Sep. 28, 1998

[51] Int. Cl.$^7$ .................................................. A01N 37/12
[52] U.S. Cl. ............................................................. 504/313
[58] Field of Search .............................................. 504/313

[56] References Cited

U.S. PATENT DOCUMENTS

| | | | |
|---|---|---|---|
| 2,603,560 | 7/1952 | Stewart | 71/2.3 |
| 2,765,224 | 10/1956 | Lambrech | 71/2.6 |
| 2,852,426 | 12/1958 | Stansbury | 167/22 |
| 2,942,023 | 6/1960 | Gordon et al. | 260/468 |
| 2,948,653 | 8/1960 | Bavley et al. | 167/22 |
| 3,143,408 | 8/1964 | Smythe et al. | 71/2.5 |
| 3,399,990 | 9/1968 | Humphrey et al. | 71/11 |
| 3,555,160 | 1/1971 | Gier et al. | 424/308 |
| 3,652,653 | 3/1972 | Emerson et al. | 504/313 |
| 3,810,750 | 5/1974 | Davidson et al. | 71/78 |
| 3,991,100 | 11/1976 | Hochberg | 260/485 |
| 4,071,348 | 1/1978 | Abramitis | 71/78 |
| 4,095,973 | 6/1978 | Maeda et al. | 71/103 |
| 4,123,552 | 10/1978 | Kensler, Jr. et al. | 424/311 |
| 5,092,918 | 3/1992 | Kuchikata | 71/94 |

FOREIGN PATENT DOCUMENTS

| | | |
|---|---|---|
| 33 21 529 | 12/1984 | Denmark . |
| 43 19 263 | 1/1994 | Denmark . |
| 2 309 904 | 8/1999 | United Kingdom . |

*Primary Examiner*—S. Mark Clardy
*Attorney, Agent, or Firm*—Locke Liddell & Sapp LLP

[57] ABSTRACT

A method for controlling undesired vegetation comprises contacting the vegetation with a herbicidally effective amount of a composition containing the compound of the formula $ROOC(CH_2)_nCOOR'$ wherein R and R' are independently selected from a $C_1$ to $C_8$ alkyl group and n is from 1 to 8.

23 Claims, No Drawings

METHOD OF USING ALIPHATIC CARBOXYLIC ACID DIESTERS AS NON-SELECTIVE HERBICIDES

FIELD OF THE INVENTION

The present invention relates to the use of aliphatic carboxylic acid diesters as non-selective herbicides to destroy the growth of plants.

BACKGROUND OF THE INVENTION

There are two major categories of herbicides to treat growing weeds—selective and non-selective. Selective herbicides only kill selected weeds such as broad leafed plants like dandelion, an example being the well-known herbicide 2,4-D. The non-selective herbicides kill all weeds. Commercially known non-selective herbicides include glyphosate (such as ROUNDUP®) and paraquat. Paraquat is a known hazardous material. Roundup often has a higher than desired kill time. Non-hazardous non-selective herbicides exhibiting decreased kill time are desired.

It is therefore a principal object of this invention to provide non-hazardous non-selective herbicides having low kill time for use on unwanted vegetation.

Other aspects and advantages of this invention will be apparent to those of skill in the art in view of the following disclosure and appended claims.

SUMMARY OF THE INVENTION

Undesired vegetation, such as weeds, grasses, moss or other plants may be killed by wetting the leaves of such plants with a carboxylic acid diester of the formula:

$$ROOC(CH_2)_nCOOR' \quad (I)$$

wherein R and R' are independently selected from a $C_1$ to $C_8$ saturated alkyl group and n is from 1 to 8. Such compounds have been found to act as "non-selective" herbicides.

The invention relates to a method for killing unwanted vegetation, by applying to the locus of the unwanted vegetation a composition containing the referenced compound. The compound may be applied neat or as a composition. The composition may contain a diluent or surfactant or combination thereof. Water emulsions or solutions of the referenced compounds are desirable. Since the mode of action appears to be through the leaves of the vegetation, there is little, if any, residual herbicidal effect in the ground. Thus, it is possible to grow desirable plants adjacent to and around the treated area.

DETAILED DESCRIPTION OF THE PREFERRED EMBODIMENTS

Unwanted vegetation may be killed by wetting the locus of the vegetation with a composition containing a carboxylic acid diester of the formula:

$$ROOC(CH_2)_nCOOR' \quad (I)$$

wherein R and R' are independently selected from a $C_1$ to $C_8$ alkyl group and n is from 1 to 8. R and R' on any given compound may be the same or different alkyl group. In a preferred embodiment, n is between 2 and 6, preferably 2 to 4, most preferably 3 to 4. The composition may further contain a diluent or a surfactant.

Highly preferred as compounds for use in the invention are those wherein R and R' are the same alkyl group. R and R' preferably are a $C_1$ to $C_6$, most preferably a $C_1$ to $C_4$, alkyl group. Particularly desirable esters are the dimethyl, diethyl, diisopropyl and dibutyl esters.

Diesters of succinic acid, glutaric acid and adipic acids are particularly preferred since their corresponding diacids are readily and easily available. For instance, such substances occur in nature. Succinic acid may be found in fungi and lichens; glutaric acid in green sugar beets and water extracts of crude wool while adipic acid is found in beet juice. In addition, adipic acid is often added to foods, such as Jello, as an acidulant. Further, such substances may be found as mixed by-products of the manufacture of nylon intermediates. Such mixtures are considered waste products and that portion that is not used to make esters for solvents or used for scrubbing flue gas from power plants is frequently burned. Further, esters of such acids, in particular the methyl esters, are relatively low cost, non-regulated solvents with low toxicity that are readily biodegradable.

The herbicidal composition of this invention may further contain a mixture of two or more of the carboxylic acid diesters referenced herein. Particularly favorable results have been seen with a mixture containing diesters of glutaric, adipic and succinic acids.

As a post-emergent, the herbicides of the invention may be applied to the locus of the unwanted vegetation neat or as an emulsion or solution.

Any solvent in which the herbicide is soluble or may be emulsified may be employed as a diluent. Suitable solvents include water or water-soluble alcohols, such as methanol, ethanol, and isopropyl alcohol, or a ketone such as acetone or methyl ethyl ketone. Such compounds further form emulsions with water.

The method of the invention may be used to control established vegetation in the vicinity of a seeded crop or in a weed concentrate area by contacting the foliage of the unwanted vegetation with the herbicidal composition. The herbicidal activity of such herbicidal compositions rapidly dissipates in the unwanted vegetation upon contact.

The herbicide is applied to the locus of the unwanted vegetation in effective amounts. Typically, where the herbicide is to be applied as an emulsion or solution, the amount of herbicide in the formulation is typically between about 5 to about 90, preferably about 10 to about 50, weight percent.

Surfactants may further be employed with the herbicidal composition. Surfactants increase the wetting ability of the composition for plant foliage and facilitate the distribution of the composition to the foliage.

Either ionic or non-ionic surfactants may be used. Illustrative of classes of stable surfactants are nonionics such as the ethylene oxides condensates such as of alkylphenols or fatty alcohols and lignosulfonates, ammonium salts of mixtures of aromatic sulphone sulphonic acids condensed with formaldehyde; anionic surfactants such as 1-hydroxyethyl-2-heptadecenyl gloxalidin as well as amine oxide surfactant. The concentration of surfactant should be at least about 0.05, generally at least about 0.1, and preferably at least about 0.2 weight percent of the herbicidal composition.

The herbicides of the invention exhibit several advantages not previously seen with other commercial herbicides. These advantages include:

More Rapid Kill Time

Vegetation usually starts to die within an hour after receiving a single application. Typically unwanted vegetation is dead in less than 24 hours. Readily obtainable herbicides require at least seven days. Further, herbicides evidencing quicker kill times in the prior art are highly toxic.

Based on Naturally Occurring Compounds

Suitable herbicides for use in the invention include several based on acids found in nature. No commercially known herbicides are based on naturally occurring compounds.

Action is Through the Leaves

In light of the quick kill time of the herbicidal compositions of the invention, reseeding can take place immediately. Most commercial herbicides must be allowed to degrade before reseeding.

Non-toxic and Biodegradable

Several herbicides within the invention, such as the dimethyl esters, are non-toxic and further are biodegradable. Most commercial herbicides are hazardous to apply.

Low Cost

The herbicides of the invention are relatively low in cost.

No Dilution or Preparation Required. Prior to treatment, it is unnecessary to dilute the herbicide. The herbicide can be applied neat.

Non-regulated Solvents

Since the herbicidal compositions of the invention employ non-regulated solvents, one would expect no restrictions on shipping or storage.

The herbicidal composition of the invention is contacted with the foliage of the unwanted vegetation by spraying or otherwise distributing the composition onto the foliage. Leaves of vegetation sprayed with herbicidal compositions of the invention usually start to shrivel or turn brown within an hour or two after application. Within 24 hours, necrosis is evident. In the case of smaller weeds such as dandelions, chickweed and other common lawn weeds, the roots of the plants also shrivel and turn brown or black within 24 hours. In no cases has it been seen that treated plants sprouted new growth.

Spraying is a preferred method of wetting the leaves. A light spray is usually sufficient to kill the plant within 24 hours at ambient temperatures above 20° C. without any additional treatment. Herbicidal effectiveness generally increases with temperature.

Weeds and grasses which have been killed by use of the herbicidal composition of the invention include quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed. Moss, small tree saplings and suckers and shoots from tree roots and tree stumps may also be controlled with the compositions of the invention.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

A mixture of approximately 20% dimethyl succinate, 60% dimethyl glutarate and 20% dimethyl adipate (sold as "DBE" by DuPont Co. and as "Santosol DME" by Solutia Inc.) was sprayed without dilution on common weeds such as dandelion, plantain, chickweed, oxalis, prostate spurge, violet, common cinquefoil, wild strawberry, purslane, carpetweed, sorrel, wild onion, nimblewill, quakegrass, Bermuda grass, crabgrass, common mallow and nutsedge. In all cases the sprayed plants died within 24–48 hours. Dandelion, plantain, chickweed, quakegrass and oxalis and others turned brown and started to shrivel within several hours. In no case did re-growth occur. Any grass in the immediate vicinity of the sprayed weeds where overspray occurred also died.

EXAMPLE 2

The same mixture used in Example 1 was sprayed on the leaves of larger plants including poison hemlock, Japanese honeysuckle, poison ivy, multiflora rose, tall buttercup, pokeweed, ragweed, wild grape and lambsquarters. All treated plants died within 24–48 hours. There was no re-growth.

EXAMPLE 3

The leaves of tree suckers sprouting from the stumps of a variety of sawed off trees were sprayed with the mixture used in Example 1. The sprouts all died within 24–48 hours and no new growth from the stumps occurred.

EXAMPLE 4

A portion of lawn about 48 square feet in size was sprayed with the mixture of esters from Example 1. The lawn turned brown overnight and was completely dead within 48 hours. The dead grass was raked up and grass seed sown. The new grass germinated and grew in the normal way.

EXAMPLE 5

A mixture of esters of succinic, glutaric and adipic acids similar to the ester mixture of Example 1 except that the esters were dibutyl esters instead of methyl esters was sprayed without dilution on a variety of weeds similar to those described in Example 1. All of the treated plants died within 24–48 hours.

EXAMPLE 6

A comparison of the efficacy of the individual dimethyl esters of succinic, glutaric and adipic acids to kill vegetation was made by spraying each of three approximately four square feet plots of weeds (crabgrass, Bermuda grass, dandelion, plantain, etc.) with one of the dimethyl esters in the ester mixture used in Example 1, i.e., pure dimethyl succinate was sprayed on one plot, dimethyl glutarate on the second, and dimethyl adipate on the third. The vegetation on the plots treated with dimethyl glutarate and dimethyl adipate turned completely brown and withered in less than 24 hours. Although some of the vegetation on the dimethyl succinate sprayed plot turned brown within 24 hours, it still contained some green color after 72 hours. A longer kill time was noted for the dimethyl succinate.

EXAMPLE 7

A 25% solution of the diester mixture described in Example 1 was made by dissolving 100 g. of diester mixture in 200 g. 70% isopropanol (commercial rubbing alcohol) and 100 ml of water. The isopropanol was required in order to get complete solution of the ester mixture in water. The solution was sprayed from a spray bottle with a fine mist on an approximately six square feet plot of weeds similar to that described in Example 7. Within 6 hours at an ambient temperature of 85° F., the sprayed vegetation had turned gray and tan with shriveled leaves. All of the sprayed plants were dead in less than 24 hours. No re-growth occurred.

EXAMPLE 8

A 10% clear solution of the diesters described in Example 1 was prepared by dissolving 50 g. of diester mixture in 200 g. of 70% isopropanol and 250 ml. of water. The leaves of the weeds on an approximately four square feet plot of weeds containing Bermuda grass, plantain, clover and dandelion were wetted with the solution by spraying from a spray bottle. Within 6 hours, at a temperature of around 80° F., all of the sprayed vegetation turned brown with the dandelion, clover and plantain completely shriveled and dead. All of the sprayed weeds were dead in less than 24 hours. There was no re-growth.

EXAMPLE 9

A 5% solution of the esters described in Example 1 was prepared by dissolving 50 g. of diester mixture in 100 g. of 70% isopropanol and 850 ml. of water and the resultant solution sprayed on a four square feet plot of weeds similar to that described in Example 8. After 24 hours all of the treated vegetation had died except the Bermuda grass which appeared unaffected.

From the foregoing, it will be observed that numerous variations and modifications may be effected without departing from the true spirit and scope of the novel concepts of the invention.

What is claimed is:

1. A method for the control of undesired vegetation which comprises applying to the locus of the undesired vegetation a herbicidally effective amount of at least one carboxylic acid diester of the formula:

$$ROOC(CH_2)_nCOOR' \qquad (I)$$

wherein R and R' are independently selected from a $C_1$ to $C_8$ alkyl group and n is from 1 to 8.

2. The method of claim 1, wherein R and R' are the same $C_1$ to $C_8$ alkyl group.

3. The method of claim 2, wherein n is 2 to 6.

4. The method of claim 3, wherein n is 3 to 4.

5. The method of claim 3, wherein R and R' are both methyl.

6. The method of claim 1, wherein the carboxylic acid diester is a mixture of two or more compounds of the formula $ROOC(CH_2)_nCOOR'$.

7. The method of claim 1, wherein the carboxylic acid diester is a mixture of esters of succinic acid, glutaric acid and adipic acid.

8. The method of claim 3, wherein the carboxylic acid diester is a succinic acid diester.

9. The method of claim 8, wherein the carboxylic acid diester is dimethyl succinate.

10. The method of claim 4, wherein the carboxylic acid diester is glutaric acid diester.

11. The method of claim 7, wherein the carboxylic acid diester is a mixture of dimethyl succinate, dimethyl glutarate and dimethyl adipate.

12. The method of claim 10, wherein the carboxylic acid diester is an adipic acid diester.

13. The method of claim 12, wherein the adipic acid diester is dimethyl adipate.

14. The method of claim 10 wherein the glutaric acid diester is dimethyl glutarate.

15. The method of claim 2 wherein the vegetation is quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed.

16. A method for the control of undesired vegetation which comprises applying to the locus of the undesired vegetation a herbicidally effective amount of a composition comprising (i.) at least one carboxylic acid ester of the formula:

$$ROOC(CH_2)_nCOOR' \qquad (I)$$

wherein R and R' are independently selected from a $C_1$ to $C_8$ alkyl group and n is from 1 to 8 and (ii.) a diluent or a mixture thereof.

17. The method of claim 16, wherein R and R' are the same $C_1$ to $C_8$ alkyl group.

18. The method of claim 17, wherein n is 2 to 4.

19. The method of claim 16, wherein the diluent is an alcohol, ketone or water, or a mixture thereof.

20. The method of claim 19, wherein the diluent is isopropyl alcohol.

21. The method of claim 20, wherein the diluent is a mixture of alcohol and water.

22. The method of claim 16, wherein the composition further contains a surfactant.

23. The method of claim 17, wherein the vegetation is quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed.

* * * * *

UNITED STATES PATENT AND TRADEMARK OFFICE
CERTIFICATE OF CORRECTION

PATENT NO.       : 6,117,823
APPLICATION NO.  : 09/162393
DATED            : September 12, 2000
INVENTOR(S)      : Robert A. Smiley It is certified that error appears in the above-identified patent and that said Letters Patent is hereby corrected as shown below:

In claim 1, before the end of the claim and after "to", please delete "8" and insert therefor --6--.

Signed and Sealed this

Seventh Day of August, 2007

JON W. DUDAS
*Director of the United States Patent and Trademark Office*